United States Patent
Crockford (12)

(10) Patent No.: US 6,591,690 B1
(45) Date of Patent: Jul. 15, 2003

(54) MATERIAL TESTING MACHINE WITH DUAL TEST SPACE AND INTEGRAL AXISYMMETRIC TRIAXIAL MEASUREMENT SYSTEM

(76) Inventor: William Crockford, 13066 S. Dowling Rd., College Station, TX (US) 77845

( * ) Notice: Subject to any disclaimer, the term of this patent is extended or adjusted under 35 U.S.C. 154(b) by 0 days.

(21) Appl. No.: 09/715,371

(22) Filed: Nov. 17, 2000

(51) Int. Cl.⁷ .............................. G01B 5/30; G01B 7/16; G01L 1/00

(52) U.S. Cl. ........................................................ 73/760

(58) Field of Search ................................ 73/760, 54.41, 73/856, 38, 859, 860, 794, 795, 796, 784, 807, 597, 32; 419/38, 42, 48

(56) References Cited

U.S. PATENT DOCUMENTS

| | | |
|---|---|---|
| 3,728,895 A | 4/1973 | Shaw |
| 4,502,338 A | 3/1985 | Smith et al. |
| 4,579,003 A | 4/1986 | Riley |
| 4,587,739 A | 5/1986 | Holcomb et al. |
| 4,615,221 A | 10/1986 | Mellor |
| 5,435,187 A * | 7/1995 | Ewy et al. ............. 73/856 |
| 5,483,836 A | 1/1996 | Kinnebrew |
| 5,493,898 A | 2/1996 | Bilkhu et al. |
| 5,741,971 A | 4/1998 | Lacy |

OTHER PUBLICATIONS

Tan Siew–Ann et al., "Behavior of Asphalt Concrete Mixtures in Triaxial Compression", Journal of Testing and Evaluation, American Society for Testing and materials, Philadelphia, US, vol. 22, No. 3, May 1, 1994; pp. 195–203.

* cited by examiner

Primary Examiner—Hezron Williams
Assistant Examiner—Charlene Dickens
(74) Attorney, Agent, or Firm—McHale & Slavin, P.A.

(57) ABSTRACT

The present invention relates to a material testing device. The device includes a load frame and pressure vessel (16) which comprises a dual test space having an open section (22) and a pressure vessel cavity (24). The pressure vessel cavity (24) accepts an axisymmetric triaxial module (18) which can be configured with or without instrumentation means (60) and with or without a mounted membrane (52). In the preferred embodiment, an actuator (40) is mounted below the open section of the load frame and a reaction rod (42) is mounted so that it extends below the top of the pressure vessel cavity. In triaxial (pressurized) testing, the specimen under test (36) is positioned by lifting with the actuator (40) until it begins loading the reaction rod (42), at which point the role of the actuator changes from specimen positioning to specimen testing. In unpressurized testing, the reaction rod (42) is adjusted downward prior to testing so that a loading fixture with a specimen in it, or a specimen without a loading fixture, placed in the open test space will begin loading the reaction rod (42) before the actuator can lift it into the triaxial test space. The membrane-mounted instrumentation means (60) may accommodate both vertical displacement transducers (76) and horizontal displacement transducers (78).

20 Claims, 12 Drawing Sheets

MATERIAL TESTING MACHINE WITH DUAL TEST SPACE AND INTEGRAL AXISYMMETRIC TRIAXIAL MEASUREMENT SYSTEM

FIELD OF THE INVENTION

This invention relates to materials testing machines, particularly to such machines which are used to measure engineering properties, and most particularly to machines for measuring uniaxial and axisymmetric triaxial loading configurations.

BACKGROUND OF THE INVENTION

Materials which have isotropic material properties, and those which have transversely isotropic properties, are often tested to quantify those engineering properties using a right circular cylindrical specimen loaded with a "triaxial" (axisymmetric) pressure cell. This type of testing is quite useful, in particular for geotechnical materials such as solid rock, soils, stabilized soils, aggregates, asphalt concrete and portland cement concrete. The concepts are applicable to a range of other materials as well, including plastics, composites, and any materials which do not have a homogeneous structure at the scale of the test specimen dimensions or which rely on external boundary conditions to retain their shape. In order to perform tests on materials such as pavement materials, one must do more than hydrostatic or proportional loading such as that suggested in U.S. Pat. Nos. 4,615,221 and 5,493,898 in terms of both loading and instrumentation.

U.S. Pat. No. 4,579,003 to Riley illustrates a useful device which combines triaxial loading with the capability to introduce direct shear to the specimen. However, in composite materials such as asphalt, the maximum size and size distribution of the aggregate strongly affect shear measurements because of their interaction with the specimen geometry, and many shear devices generate stress fields during loading that are functions of the material properties of the specimen which are the subject of the testing, and therefore cannot directly produce accurate measurements of those properties. While "confined" (i.e. pressurized) and "unconfined" (i.e. unpressurized) tension and compression tests e.g. those tests in which the stress applied along the direction of the axis of the cylinder is greater than the all around confining pressure, a condition which results in the engineering terminology describing the axial stress being the "major principal" stress, the cyclic portion of which is also termed "deviatoric", and the radially inward stress resulting from the simultaneous application of confining pressure being termed the "minor principal" stress, are the most common types of tests conducted in the axisymmetric triaxial configuration, it is obvious that it is difficult, if not impossible, to conduct tension tests on materials with little or no cohesion.

In the compression test, the stress is applied toward the mid-height of the specimen, but in the tension test, the stress is applied away from the mid-height which requires some technique for attaching the loading system to the ends of the specimens and such attachment is virtually impossible for many soils and aggregates. For these materials, which include many soils and aggregates, another type of test in which the major principal stress direction is changed from being applied along the axial direction, e.g. vertical in the usual orientation, to the horizontal direction, e.g. radially inward toward the center of the specimen under test, is useful. This test is referred to as an "extension" test in engineering terms and is conducted with the major principal stress direction radially inward (or horizontal in the usual configuration) and the minor principal stress direction is applied in the compression direction along the axis of the specimen. The extension test often yields engineering property data which might help understand tension behavior of the material without actually conducting a tension test, and anisotropic behavior without incurring the complexity of true three-dimensional testing on a prismatic specimen.

The instrumentation in the standard geotechnical triaxial cell has been a persistent problem in the prior art. While useful for rock specimens, instrumentation solutions such as that given in U.S. Pat. No. 4,587,739 do not work for low cohesion materials such as soils, road base materials and hot asphalt concrete in part because the devices often have high localized stress fields at the specimen contact points in order to support the mounting system. Ultrasonic testing systems such as that given in U.S. Pat. No. 5,741,971 suffer from difficult analysis procedures required to accurately quantify the properties of particulate materials, and the extrapolation of the results from the test's high frequencies down to relevant frequencies for time-dependent and stress-dependent pavement materials is sometimes ineffective.

Some cohesive and engineered geotechnical materials are also tested using beam flexure and indirect tension loading (e.g. Standard Test Method for Indirect Tension Test for Resilient Modulus of Bituminous Mixtures by ASTM in ASTM D4123 (Apr. 30, 1982), Resistance of Compacted Bituminous Mixture to Moisture Induced Damage by AASHTO in AASHTO T283 (1989), and Resistance to Plastic Flow of Bituminous Mixtures Using Marshall Apparatus by AASHTO in AASHTO T245 (1994)), both of which general categories of test are usually performed without confining pressure.

There are two major categories of axisymmetric triaxial pressure cells. In the first type of triaxial cell (e.g. Standard Test Method for Determining the Resilient Modulus of Soils and Aggregate Materials by AASHTO in AASHTO TP46 (T294) (1994), Resilient Modulus of Subgrade Soils and Untreated Base/Subbase Materials by AASHTO in AASHTO T292 (1991)), the specimen is capped, placed in a rubber membrane, and is surrounded on all sides, top, and bottom by a confining medium inside the cell (usually air, water, or oil, the fluid obviously being selected based upon the necessary thermal, mechanical, and electrical conductivity requirements of the particular application). This configuration is termed the "standard geotechnical" configuration throughout the instant disclosure. When pressure is applied all around the specimen through the confining medium alone, a hydrostatic stress state is said to exist.

In order to evaluate material properties at a constant confining pressure, the stress along the axis of the specimen is usually changed dynamically (i.e. cyclically) through a sealed linear bearing by an actuator shaft reacting against a load frame external to the triaxial cell. This dynamic action is usually referred to as a deviatoric stress and the direction of application is usually the major principal stress direction. In some systems, the confining pressure may also be changed dynamically. Usually, the specimen deformation instrumentation associated with this configuration is either outside the cell or referenced to some relatively rigid component of the cell such as the base plate.

DISADVANTAGES OF THIS BASIC CONFIGURATION INCLUDE 1. the direction of the major dynamic deviatoric stress cannot be altered from the axial direction without sophisticated analysis and control systems which enable the axial actuator to counteract the change in the axial component of the dynamically changing hydrostatic pressure, also taking into consideration (a) the frictional effects of the pressure sealed linear bearing which is necessary if the load measuring device is located outside the triaxial cell and (b) the applicable cross sectional area of the loading shaft and platen assembly, factors (a) and (b) above being addressed to a certain extent by U.S. Pat. Nos. 4,679,441 and 5,435,187;

2. measurement devices which bear on the confining medium side of the membrane must have their measurements adjusted for the expected deformation of the membrane when subjected to a pressure change;

3. local specimen inhomogeneities (e.g. rocks with adjacent voids), normal specimen bulging in compression and normal necking in tension or extension cause inaccuracy with externally referenced instrumentation devices (i.e. the deformation along the sensitive axis of the instrumentation sensor cannot be separated from the deformation in another direction that occurs due to behavior such as bulging and necking);

4. externally referenced axial instrumentation devices (e.g. an axial measurement taken from the loading platen or actuator shaft) cannot separate specimen end effect deformations from the prevailing strain field in the middle portion of the specimen;

5. externally referenced radial instrumentation devices must incorporate sensors that are provided in pairs so that specimen translation (e.g. tilting due to ends that are not parallel) can be separated from radial strain which is internal to the specimen;

6. externally referenced radial instrumentation devices that are mounted "through-the-wall" (i.e. mounted in the wall of the pressure vessel) are susceptible to critical measurement errors because any strain in the wall of the pressure vessel during testing cannot be directly separated from the strain in the specimen;

7. heretofore, attempts to measure radial strain have used devices that are either referenced to a cell component such as the base plate or use constrictors such as springs to support the weight of the devices as well as provide the necessary tension to return the sensitive components of the sensor to proper position;

8. the use of constrictors to perform the dual functions mentioned above often results in erroneous measurements because the constrictor is often so strong that it restricts the lateral movement of the specimen under load so that a true picture of the deformation is not achieved;

9. an alternative solution to the radial strain measurement problem is to measure the vertical strain and the volume change of the fluid, but this approach is very susceptible to dissolved gas in the fluid, gas that could not be removed from hidden pockets in the cell prior to testing, and membrane deformation;

10. the process of filling and draining the triaxial cell and adjusting the instrumentation for each test is extremely tedious and time consuming.

The second type of triaxial cell is the Texas triaxial type found in Triaxial Compression Tests for Disturbed Soils and Base Materials by Texas DOT in Tex-117-E (1991), which solves some of the problems inherent in the standard geotechnical cell described above. Specifically, it solves, conceptually at least but not practically, the problem of requiring sophisticated systems to change the direction of the major deviatoric stress. This is made possible because the confinement is only applied in the radial direction and the axial load is a completely separate applied stress. It is a significantly simpler matter to conduct an extension test in this type of triaxial cell than in a standard geotechnical cell. In contrast to the standard geotechnical cell, it also has the advantage for production testing of cohesive materials that the membrane is part of the cell, not a consumable part of the specimen assembly requiring a tedious installation process prior to placing the assembly inside the cell.

However, disadvantages of the Texas triaxial type of cell include:

1. it is functionally limited to low stress levels and monotonic loading, especially with respect to the confinement because gas is used as the confining medium, the volume to be compressed is large, the confining pressure is controlled by a manual valve, the pressure vessel is a thin wall tube, and the membrane attachment detail allows two free membrane surface areas to expand and contract causing large fluctuations in the size of the volume required for pressurization and depressurization, which, in turn eliminates efficient dynamic response regardless of the confining medium being used;

2. there is no deformation measurement system, so the device can only be used for strength testing which only requires a load measuring device.

A triaxial cell similar to the Texas triaxial type is the Hveem stabilometer illustrated in Standard Test Methods for Resistance to Deformation and Cohesion of Bituminous Mixtures by Means of Hveem Apparatus by ASTM in ASTM D 1560 (Nov. 27, 1981) and Mechanics, Operation, Calibration, and Diaphragm Installation of the Stabilometer by California DOT in CalTrans 102 (1978). The Hveem stabilometer improves upon the Texas triaxial cell in the area of the membrane attachment detail, wherein it effectively reduces the free membrane surface area.

The Hveem stabilometer includes the following disadvantages:

1. the pressure is applied to the membrane using a manual crank, which eliminates the possibility of practical dynamic response;

2. a fluid is used as the confining medium, but the measurements are extremely sensitive to entrapped air, and the casting and assembled components of the cell make it difficult to purge air from the system for calibration purposes;

3. the device does not measure engineering properties which independently characterize the material behavior, it measures a test property which can only be used for comparing materials tested in the same apparatus or must be correlated with engineering property measurements to indirectly infer properties of materials which have not been tested for true engineering properties.

SUMMARY OF THE INVENTION

The instant invention teaches a material testing machine comprising dual test spaces, one for unpressurized specimen testing and one for pressurized axisymmetric triaxial testing. The pressurizable test space is adapted to accept a triaxial testing module, said triaxial testing module either comprising sealing components that enable the pressure vessel to emulate a standard geotechnical type pressure vessel, or a rapid operating triaxial cell module comprising sealing components and a membrane which may be optionally instrumented for axial and/or radial strain measurement.

It is an objective of the instant invention to provide a material testing machine which obviates the disadvantages of prior machines by being compact in size, thereby enabling it to be used in crowded laboratories or for mobile applications.

It is another objective of the instant invention to provide a material testing machine which has a dual test space, one of which can be configured for either standard geotechnical triaxial testing or for rapid triaxial testing using an integral reusable membrane and a membrane-mounted displacement measurement system configurable for axial, radial, or combined radial and axial measurements.

It is still another objective of the instant invention to provide a material testing machine which can be made relatively economically, and which can be easily operated, said testing machine comprising a loading reaction frame that is also a pressure vessel over a portion of its length thus eliminating the need for a separate loading frame and additional triaxial test fixture that must be mounted in the frame, and which further is constructed and arranged to have an open test space over the remaining portion of its length configurable for use with additional separate test fixtures commonly used in the prior art.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
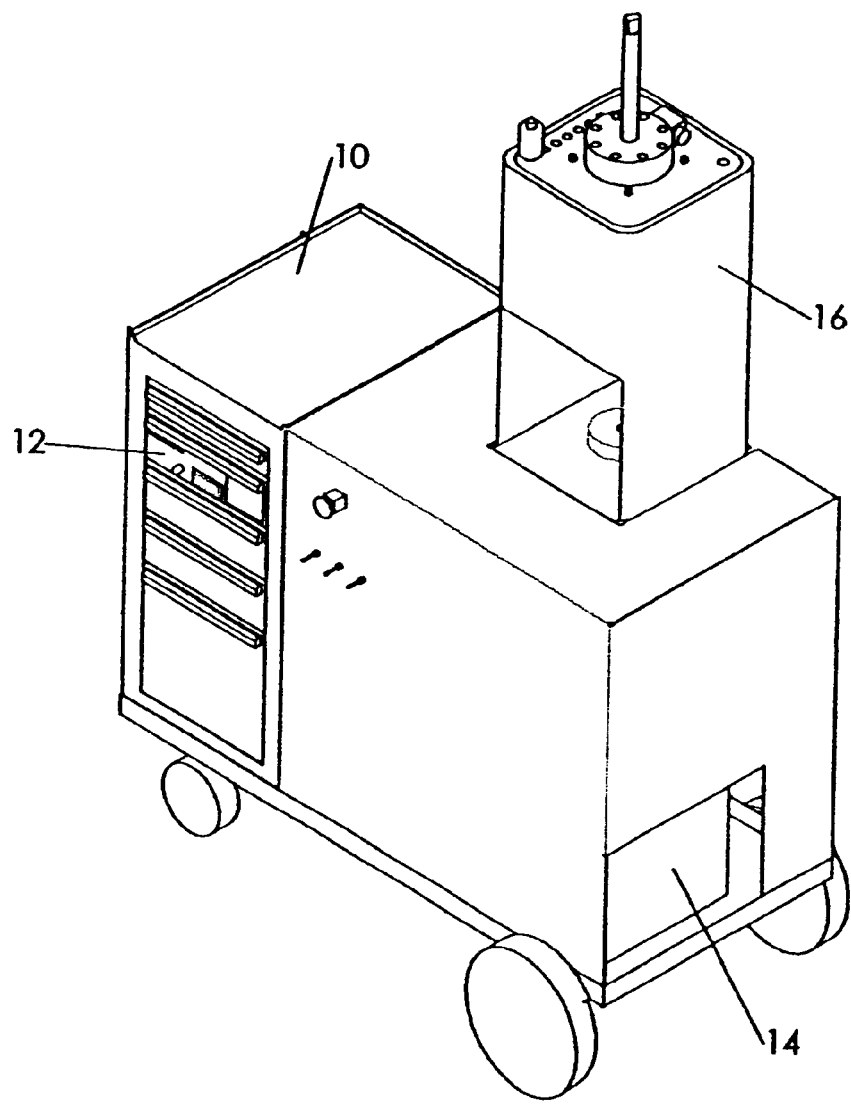
FIG. 1 is an overall perspective view of a testing device in accordance with the instant invention.

With reference to FIG. 1, an overall perspective view of a testing machine in accordance with the instant invention is illustrated. The machine is shown as being installed in a compact mobile cart 10 which may house, separately or in combination, electronic components 12, and mechanical, and fluid/gas components 14 typically used to power and control the invention and acquire data from the invention.

Figure 2:
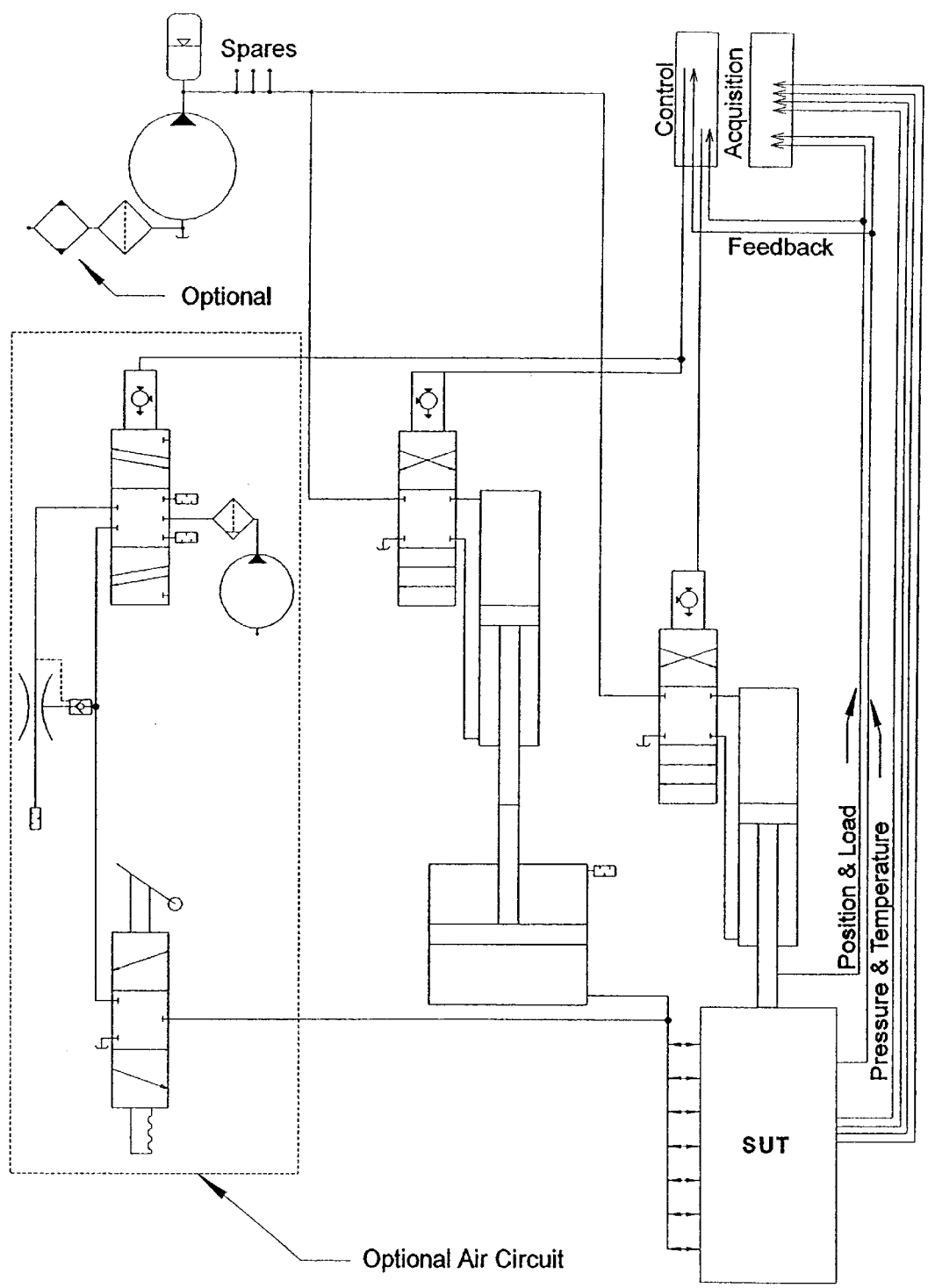
FIG. 2 is a schematic of a hydraulic and/or pneumatic control circuit useful in combination with the subject invention.

FIG. 2 shows a schematic of a prior art hydraulic control circuit, useful separately or in combination with a pneumatic control circuit method that is useful to operate a testing machine in accordance with the instant invention.

Figure 3:
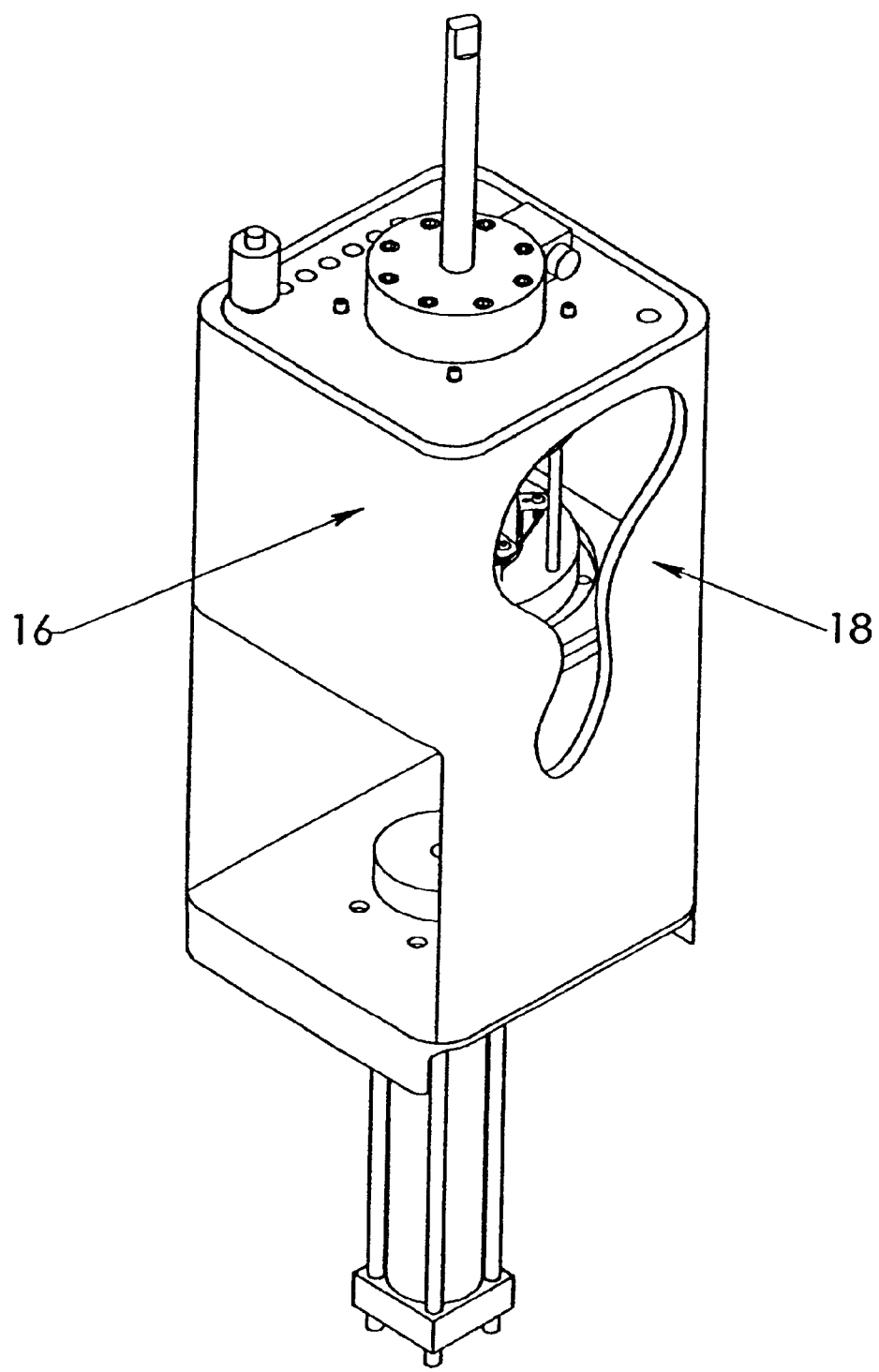
FIG. 3 is an overall perspective view of a testing machine according to the invention.

Now referring to FIG. 3, an overall perspective view of a testing machine according to the invention is illustrated. The machine comprises two major assemblies, a load frame and pressure vessel 16 in combination, and, partially visible through the cutaway section in the pressure vessel in FIG. 3 and shown in detail in FIG. 5, an axisymmetric triaxial assembly 18, preferably of the "rapid" type, the type descriptor referring to one significant operating advantage over the prior art's standard geotechnical triaxial cell.

Figure 4:
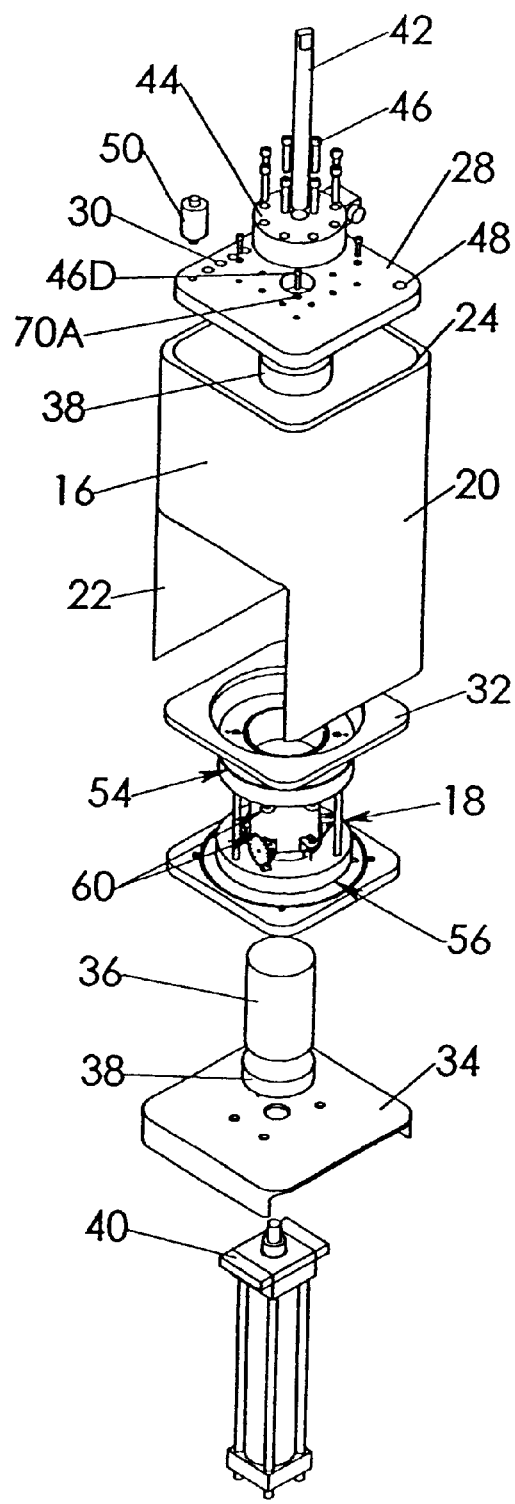
FIG. 4 is a partially fragmental view of the combined load frame and pressure vessel, expanded parallel to the central vertical axis of the specimen under test.

FIG. 4 illustrates an exploded view of the load frame and pressure vessel 16 in combination. The main structural component is a single tube 20, preferably made of steel, machined such that there is an open section 22 over a portion of its length. The top end of the tube which retains the full closure of the pressure vessel cavity 24 is sealed with a top plate 28, preferably by welding said plate to the interior periphery of the tube. This top plate preferably acts as the upper load reaction member and bulkhead through which pressure-proof electrical measurement transducer connections 30 are made (e.g. using Lemo U.S.A., Inc. Model EGG.1K.306.CLL light duty pressure connectors). A module attachment plate 32 is preferably welded to the interior periphery of the closed cavity above the open section. A base reaction member 34 is preferably welded to the lower ends of the open section. The specimen under test (SUT) 36 is axially loaded through a pair of platens 38, one of which is preferably attached to a loading device which, in the preferred embodiment, is a hydraulic actuator 40, however the invention is not limited thereby.

Figure 12:
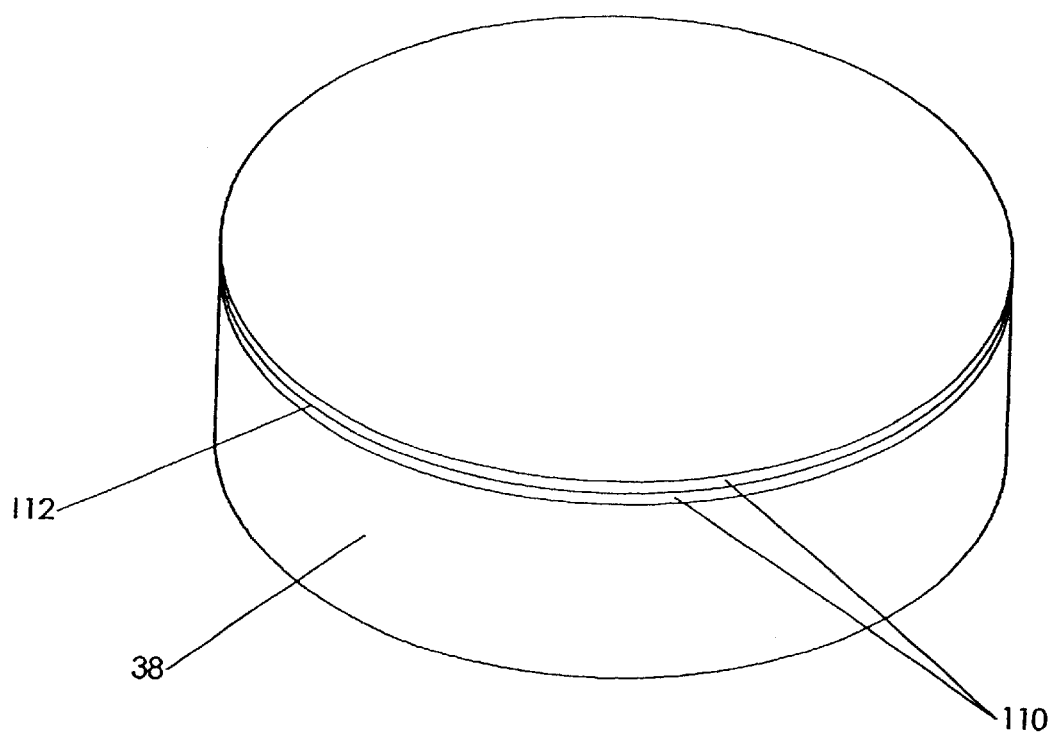
FIG. 12 is a perspective view of a brush platen.

The platens 38 are depicted as solid pieces that would normally be machined from metals such as steel or aluminum. There are advantages to using a platen system that has been described in the prior art as a "brush" platen because it is relatively stiff in the axial direction and less stiff in the radial direction (similar to the bristles on a brush), FIG. 12. While this set of transversely isotropic material properties can be engineered into various types of composite materials, the same effect can be attained by attaching a facing material to the platen. The objective is to face the metal platen where it interfaces with the flat end of the specimen under test 36 with a material that has a lower coefficient of friction and/or is soft enough to expand with the material of the specimen under test 36. The reason it is desirable to let the surface of the specimen expand is that it reduces "end effects" which tend to make the specimen "barrel" in the center under axial loading (i.e. the specimen under test 36 might take on the shape of a whiskey barrel). The barrel shape makes accurate determination of the radial and axial strains more difficult. A thin sheet 110 of material that has a Poisson's ratio close to 0.5 will work for this application. Natural and synthetic rubber have been found to work for this application as has PTFE. The stiffness in the axial direction is basically a by-product of the fact that the material is usually a relatively thin sheet that is backed by the stiff metal platen. FIG. 12 shows an application of the brush platen concept that utilizes more than one sheet. In this application, a lubricant or fluid 112 may be introduced between the two sheets in order to enhance the anisotropic behavior of the facing system (i.e.

enable relatively large radial deformation for small vertical deformation). This system cannot be used when axial displacement measurements are taken across the platens instead of across some gauge length within the length of the specimen. The reason for this limitation is that the axial deformation of the sheet material cannot be directly isolated from the axial deformation in the specimen under test 36 and the strain measurements will therefore be incorrect. The sheet(s) 110 may be introduced without attachment to the platen, mechanically attached to the platen, or attached using an adhesive ring around the periphery of the piece(s). In order for the brush platen system to properly function, the diameter of the platen system must be larger than the initial (unloaded) diameter of the specimen under test 36. The anisotropic brush platen idea which is meant to reduce mechanical barreling of the specimen under test 36 is the subject of the article in Texas Transportation Institute, NCHRP 386, Design and Evaluation of Large-Stone Asphalt Mixes, 1997, page 9 of 141 pgs. The use of insulating material for the brush platen facing and/or control of the temperature of the facing material or of an interface fluid between the sheets for the purpose of maintaining the temperature of the specimen under test 36 by stopping heat transfer through the platens, separately or in combination with controlling the temperature of a fluid in the pressure vessel cavity 24 is considered a novel embodiment over that which is taught or suggested in the prior art. The operation of the brush platen is not significantly different from the operation of the preferred embodiment. The actuator 40 may be of a different type such as pneumatic or mechanical. However, hydraulic actuators minimize the compressibility and speed limitations inherent in these alternative embodiments. The other platen is preferably attached to a reaction rod 42, said reaction rod transferring the load to a load measurement transducer 44 such as an electronic load cell or a mechanical proving ring. Reaction rod 42 is shown in the preferred embodiment as a manually adjustable rod. This may be automated using other means such as electrohydraulic or electromechanical means. Operation with automated means is not significantly different from that given in the preferred embodiment.

The load measurement transducer 44 transfers the axial load to the top plate 28 through attachment means such as screws 46. Inlet and outlet ports 48 are provided in the top plate 28 for pressurizing and depressurizing the pressure vessel cavity 24. A pressure measurement transducer 50 is preferably mounted on the top plate 28.

The preferred embodiment comprises three vertical transducers set 120 degrees apart in planform, and two horizontal transducers spaced vertically. The inventor considers three vertical transducers and six mounting points to be optimal, but does not wish to be bound by this. While a reduction to two vertical transducers located at 180 degrees apart is viable with either four or eight mounting points, it is not preferred because of potential problems with measurement accuracy. Additional vertical transducers above the preferred number of three are viable and would tend to increase confidence in the measurement, but such an embodiment will incur significant additional costs to manufacture.

In general, three mounting points at 120 degrees apart, and four mounting points at 90 degrees apart are considered to be too few because, for many commonly used specimen diameters, the mounts would need to extend larger distances from the surface of the specimen, requiring greater mass for the mount and a longer arm through which the self-weight of the mount acts likely increasing the force required to be transmitted through the flexible cable.

A single horizontal transducer at the mid-height of the SUT 36 instead of two, one at each end of the vertical gauge length, is a viable option. If the single horizontal option is selected, the mounting points should preferably be provided with a through clearance hole so that the vertical transducers may pass through unhindered. This feature could increase the accuracy of Poisson's ratio measurements since the horizontal measurement is being taken along the same vertical line as the vertical measurement. In the single horizontal transducer arrangement, the upper and lower mount system should preferably be provided with a flexible cable just as in the preferred embodiment so that moments may be reduced.

Reduction to zero transducers is a viable option, but not generally of practical utility.

There is no significant difference in operation of the invention with alternative embodiments having a number of transducers different from the preferred embodiment. However, the operator must rederive the equations for radial strain taking into account the different number of points about which flexible cord 80 must travel.

Figure 5:
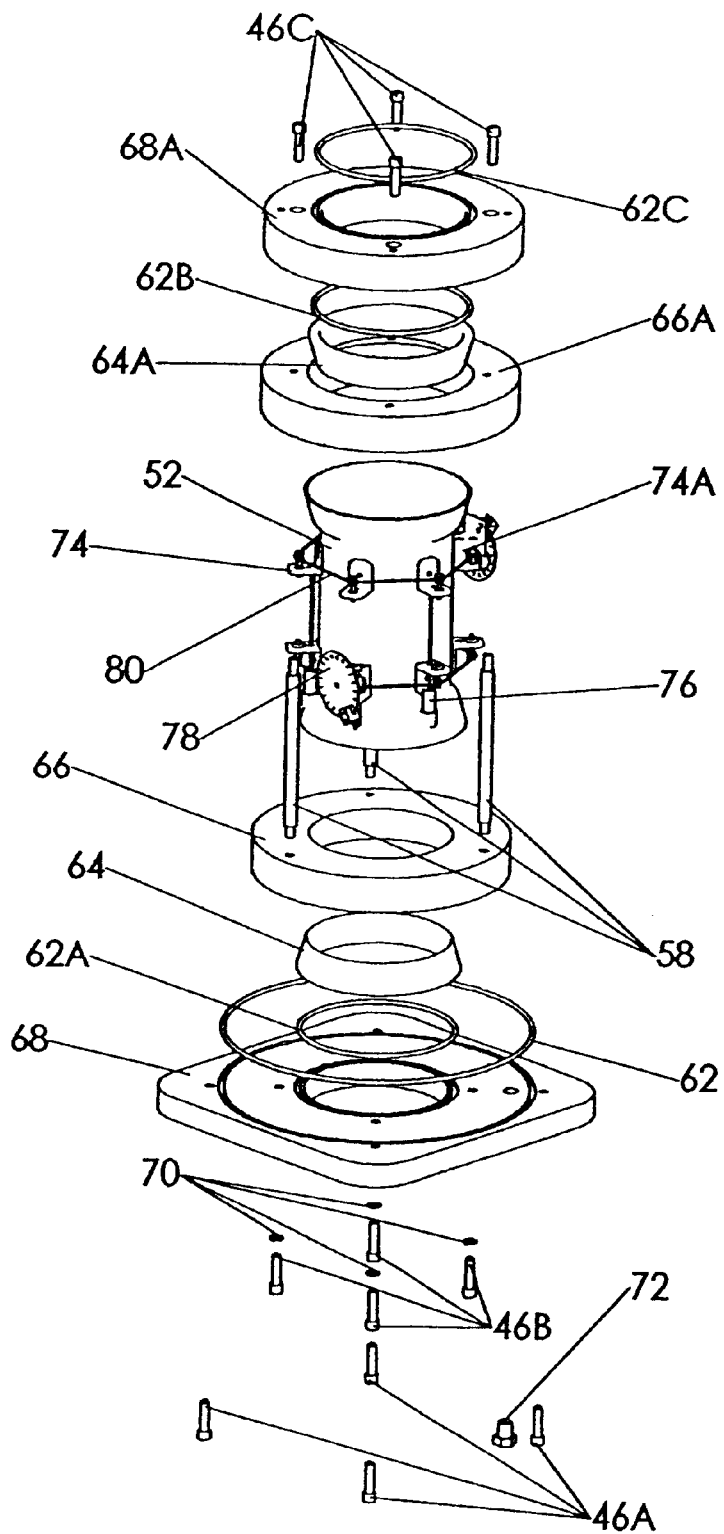
FIG. 5 is a partially fragmented view of the rapid triaxial module according to the invention exploded along the central axis of the cylindrical cavity.

Now referring to FIGS. 4 and 5, the rapid axisymmetric triaxial assembly 18, comprises a membrane 52, preferably constructed of silicone rubber or other natural or synthetic elastomer, an upper sealing ring assembly 54, a lower sealing ring assembly 56, spacer rods 58, and instrumentation means 60. The axisymmetric triaxial assembly 18 can be removed from and installed in the pressure vessel cavity 24 as an assembled unit, said installation being preferably accomplished with screws 46A and pressure sealing preferably accomplished with an O-ring 62. The lower sealing ring assembly 56 comprises a taper ring 64, a taper ring seat 66, and a lower retainer 68. The pressure seal for this lower sealing ring assembly 56 comprises the membrane 52 and captive washer seals 70 (e.g. "STAT-O-SEAL" or "LOCK-O-SEAL" products of the Parker-Hannifin Corporation, Seal Group) on screws 46B which, when tightened, simultaneously apply a sealing crush on the membrane 52, the captive washer seals 70, and the O-ring 62A. The retainer 68, is preferably drilled and tapped to receive a plug 72 or drain valve. The upper sealing ring assembly 54 comprises a taper ring 64A, a taper ring seat 66A, and a retainer 68A. When tightened, screws 46C, simultaneously apply a sealing crush on the membrane 52, and the O-ring 62B. An O-ring 62C and captive washer seals 70A provide a pressure seal between the retainer 68A and the top plate 28 when screws 46D are tightened. Spacer rods 58 are preferably mechanically attached (threaded) to the lower taper ring seat 66 and made for a sliding fit in alignment holes in upper taper ring seat 66A. The instrumentation means 60 preferably comprise mounts 74 for vertical displacement transducers 76 (e.g. linear variable displacement transducers, "LVDTs"), mounts 74A for moving element of the horizontal displacement transducers 78 (e.g. rotary encoder), and flexible cord 80 (e.g. SPECTRA cable of the Allied Signal Corporation) to transfer radial displacements in the specimen under test 36 into measurable movement. Transfer of vertical displacements in the specimen under test 36 is accomplished by friction between the membrane 52, a contact disk 82 (FIG. 6), and the specimen under test 36.

Figure 6:
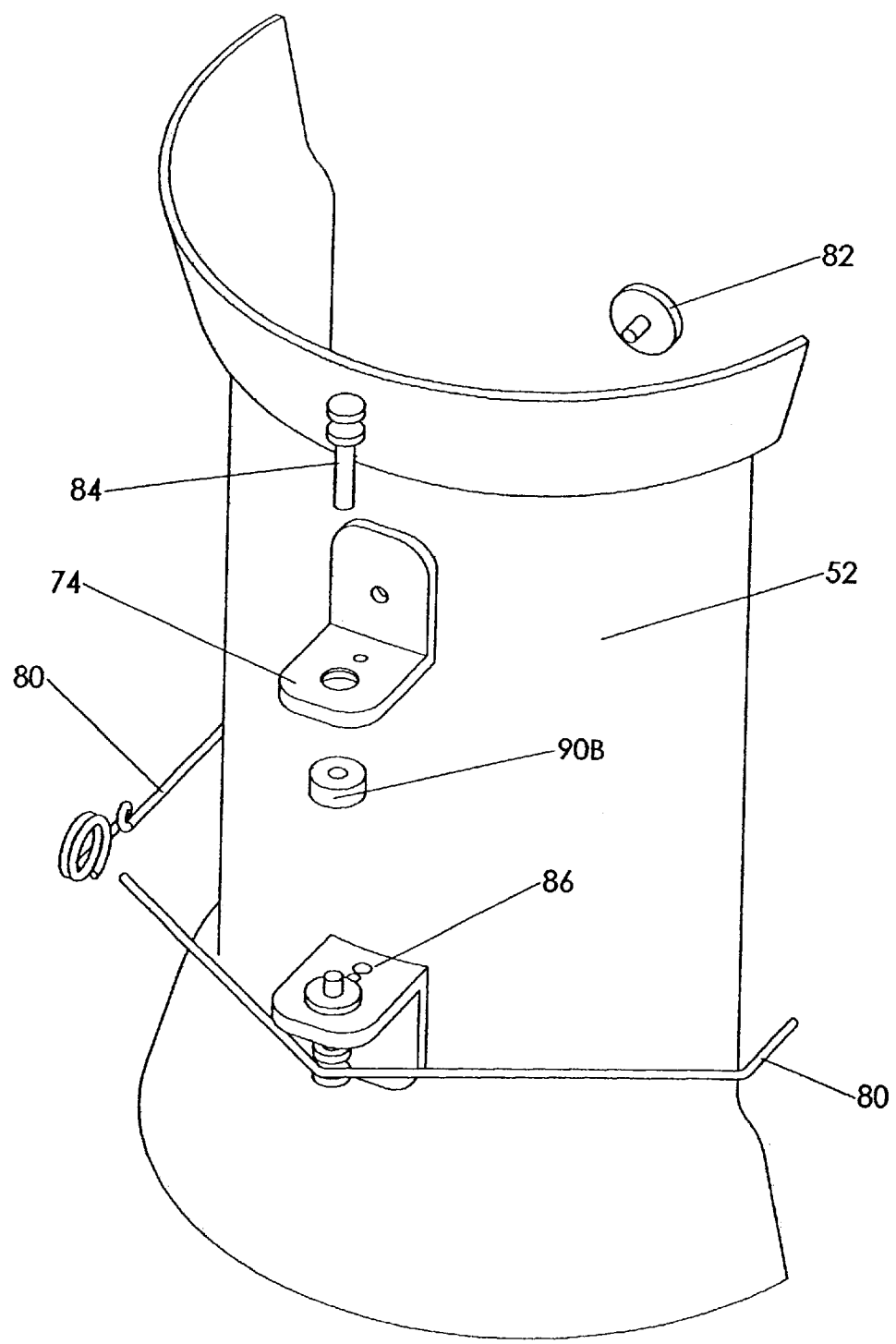
FIG. 6 is an enlarged, fragmented perspective view of a typical pivot mount.

FIG. 6, is illustrative of the pivot mount detail wherein mounts 74, in which it is feasible to insert a pivot means 84 which provides alignment and bearing point(s) or surface(s) for the flexible cord 80. The pivot 84 may be mounted in a bearing 90B. The mounts 74 are preferably attached to the membrane with contact disk 82. The contact disk 82 when tightened on the mounts 74 through the membrane 52 creates a crush pressure seal on said membrane 52 and provides a point of direct contact on the specimen under test 36. The surface perimeter of the contact disk 82 when mated with the mounts 74 preferably should not extend out past the surface perimeter of the mounts 74. This geometric preference is important for operational reasons. Mounts 74 which incorporate both a pivot 84, and a means to mount vertical displacement transducers 76 preferably implement said mounting means by a conical bearing dimple 86. The vertical displacement transducers 76 may be mounted to the mounts using a variety of methods. One option is to allow the mount to rotate with respect to the transducer as shown in the preferred embodiment. In this configuration, bulging of the specimen does not apply moments to the transducer. A second option is to provide a rigid connection between the transducer components and the mount, which may cause undesirable moments to be applied to the transducer components during testing. A third option is to use non-contact sensors, which are generally more expensive than typical contact sensors and may or may not be sensitive to rotation of the target. In all cases, it is preferable to mount the transducer as close to the specimen surface as possible.

Operation of alternative mounting embodiments is not significantly different from the preferred embodiment, except as previously noted.

Figure 7:
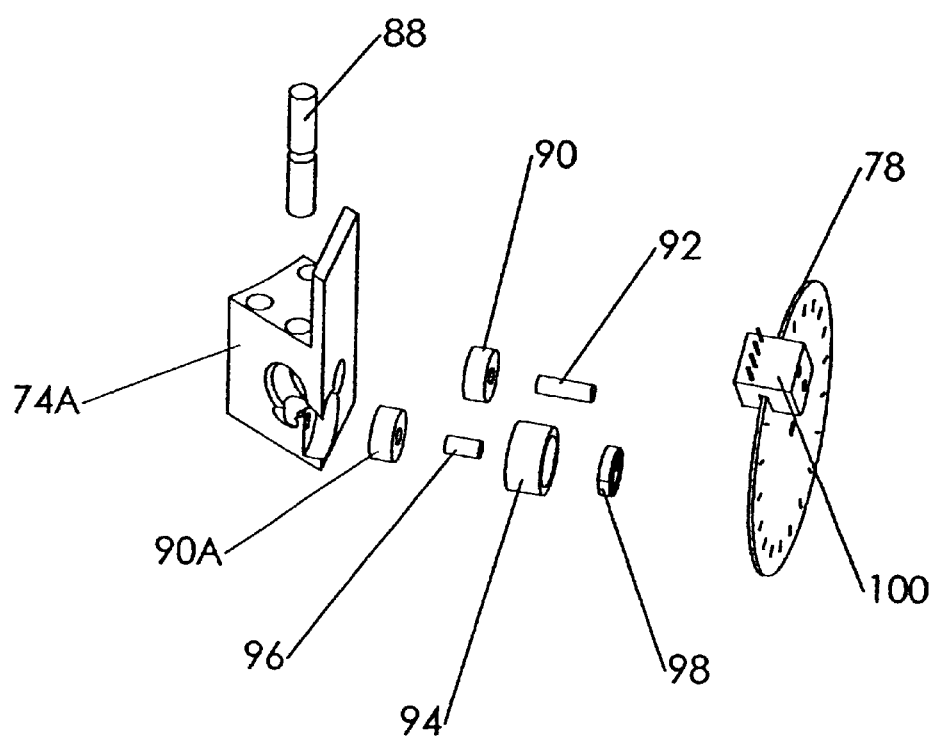
FIG. 7 is an enlarged, fragmented view of the radial displacement transducer mount.

FIG. 7 illustrates the radial transducer mount detail, wherein mounts 74A comprise the mounting structure, an anchor means 88 for anchoring one end of the flexible cord 80, a bearing 90 for a moving element of the horizontal displacement transducer 78, an axle 92 for attaching the moving element of said horizontal displacement transducer 78 (e.g. the CODEWHEEL, HEDG-61XX of Agilent Technologies of Hewlett-Packard) to the bearing 90 and for providing a frictional bearing surface around which the flexible cord 80 is wrapped, a bearing 90A which provides a moving element to which a barrel 94 is press fit, a fixed arbor 96, preferably a constant force or alternatively a power spring 98 (e.g. a watch mainspring), and the sensing element 100 (e.g. HEDS-973X of Agilent Technologies of Hewlett-Packard) of the horizontal displacement transducer. The barrel 94 provides a surface about which the remaining end of the flexible cord 80 is wound. The diameter of the barrel 94 is preferably much larger than the diameter of the axle 92. This relative diameter relationship is important for operational reasons.

Illustration of the Operation of a Preferred Embodiment of the Invention

The invention functions during testing effectively as follows:

A control system, which is not the subject of this invention, for example a system as generally described in FIG. 2, is used to control the position of hydraulic actuator 40 to apply an axial load to the ends of the specimen under test 36, while a horizontal (radial) pressure is applied to the cylindrical surface of the specimen under test 36. In response to these stresses (or induced displacements), the specimen experiences a resultant vertical strain and a radial strain. These strains are measured in the form of displacements by the vertical displacement transducers 76 and horizontal displacement transducers 78.

In addition to its function during axisymmetric triaxial testing, the hydraulic actuator 40 effectively functions as a lifting and lowering device to raise and lower the specimen under test (SUT) 36 from the loading position prior to the test in the open section 22, to the testing position in the pressure vessel cavity 24, and back to the loading position for removal after testing. By adjusting the reaction rod 42 downward and locking in place at a lowered position, alternative testing fixtures, which are not the subject of this invention, may be used for unconfined testing in the open section 22 of the load frame and pressure vessel 16. Reaction rod 42 has an additional function in the axisymmetric triaxial testing position (i.e. raised). In this position, after an axisymmetric triaxial test, the reaction rod 42 may be used to force the SUT 36 out of the pressure vessel cavity 24 if said specimen will not freely come out of the cavity when the hydraulic actuator 40 is retracted to the down position. Because the pressure vessel cavity 24 is sealed relative to atmospheric pressure, a reduction in the volume of the fluid in the cavity (or a reduction in pressure below atmospheric) will cause the membrane 52 and instrumentation means 60 to be retracted away from the cylindrical surface of the specimen under test 36. This action will allow the specimen under test 36 to be freely raised into and lowered from the pressure vessel cavity 24. During this retraction process, and during large strain testing, the flexible cord 80 may cause several rotations of the barrel 94 and the moving element of the horizontal displacement transducer 78, and this movement is an important reason for using a device such as a rotary encoder instead of an LVDT for the radial transducer in the preferred embodiment.

During initial setup and repair, the upper shoulder of the spacer rods 58 provide an initial spacing between the upper sealing ring assembly 54 and lower sealing ring assembly 56 for installing the membrane 52 and instrumentation means 60. When the finished axisymmetric triaxial assembly 18 is installed in the pressure vessel cavity 24, the upper sealing ring assembly 54 is drawn up against the top plate 28 by the screws 46D. The spacer rods 58 act as positioning reference guides during this process and as the screws 46D are tightened, the membrane 52 is slightly tensioned.

Figure 8:
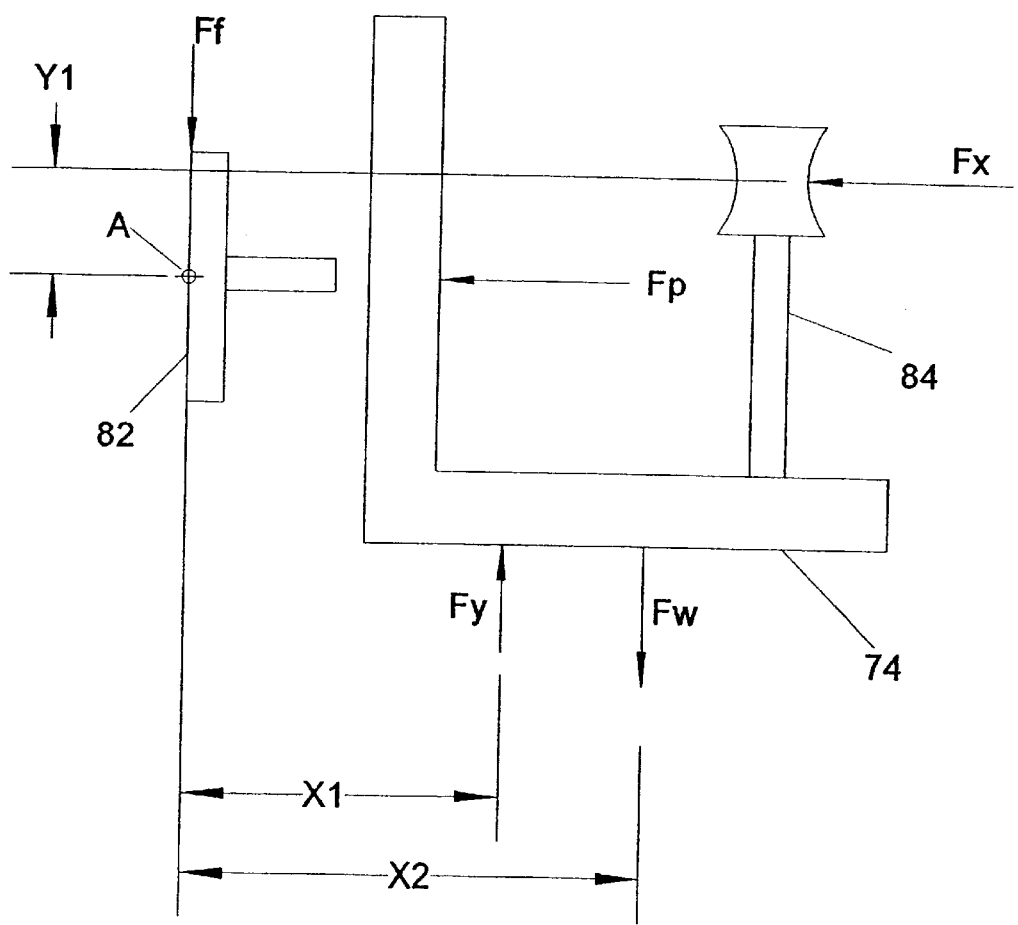
FIG. 8 shows a typical moment diagram for the forces acting on a mount of the type shown in FIG. 6.

FIG. 8 illustrates the forces acting on a typical mount 74 illustrated in sectional view. The following logic applies by obvious extension to mounting configurations other than the basic shape and design of mount 74.

The objective of the mount assembly functional design process is to design the mount and its mated components such that the moment about the point A, $M_A$, said point being located at the center of the contact disk 82 on the surface of said disk in contact with the specimen under test 36, is minimized. When a pressure is applied to the pressure vessel cavity 24, a resultant force, $F_P$, on the mount may be computed as the pressure times the surface area of the mount. The vertical location of the point of application of this force is through A when the mount is designed as shown in FIG. 8. However, by altering the vertical location of the attachment point of the contact disk 82, the applied pressure may be used to develop a moment over an arm and computation of such moment is easily calculated. The configuration of FIG. 8 has an arm of zero length applied to the resultant force of the applied pressure, so the total moment resulting from $F_P$ is zero in this example case. Likewise, the friction, $F_F$, at the specimen-disk interface acts through point A, resulting in a zero length arm, so the total moment resulting from this force is zero in the configuration of FIG. 8. In FIG. 8, there are three forces which induce non-zero moments about A. These are: $F_Y$ acting through arm $X_1$, $F_W$ acting through arm $X_2$, and $F_X$ acting through arm $Y_1$. In the configuration shown, $F_Y$ is a force due to some feature of the vertical displacement transducer 76 (e.g. a downward-acting weight of the core assembly if rigidly fixed, or an upward-acting force if not rigidly fixed but spring-loaded). $F_W$ is the self-weight of the mount, and $F_X$ is the force that is resolved through contact with the flexible cord 80 and is a function of the force generated by spring 98 and the geometry of the instrumentation means 60. The equation for the configuration illustrated in FIG. 8 is:

$$\Sigma M_A = F_Y X_1 + F_X Y_1 - F_W X_2$$

which, when set to zero becomes:

$$F_Y X_1 + F_X Y_1 = F_W X_2$$

Since $F_W$ and $F_Y$ are known once the basic mount design and instrumentation specifications have been finalized, and since $X_2$ is known based on the design of the mount, the distances $X_1$ and $Y_1$ and the force $F_X$ are the variables that may be used to design for zero moment. Since $X_1$ may have a limited range over which it may be varied due to physical factors, the primary variables that can be used for design are $Y_1$ and $F_X$. It is generally desired to minimize $F_X$ as much as feasible, so $Y_1$ becomes the major variable of interest. It is obvious that by increasing or decreasing $Y_1$, the moment resulting from $F_X$ may be increased or decreased, even decreased to a negative value indicating a contribution to the overall moment in the opposite direction from a counterclockwise positive sign convention used in the above computations.

Figure 9:
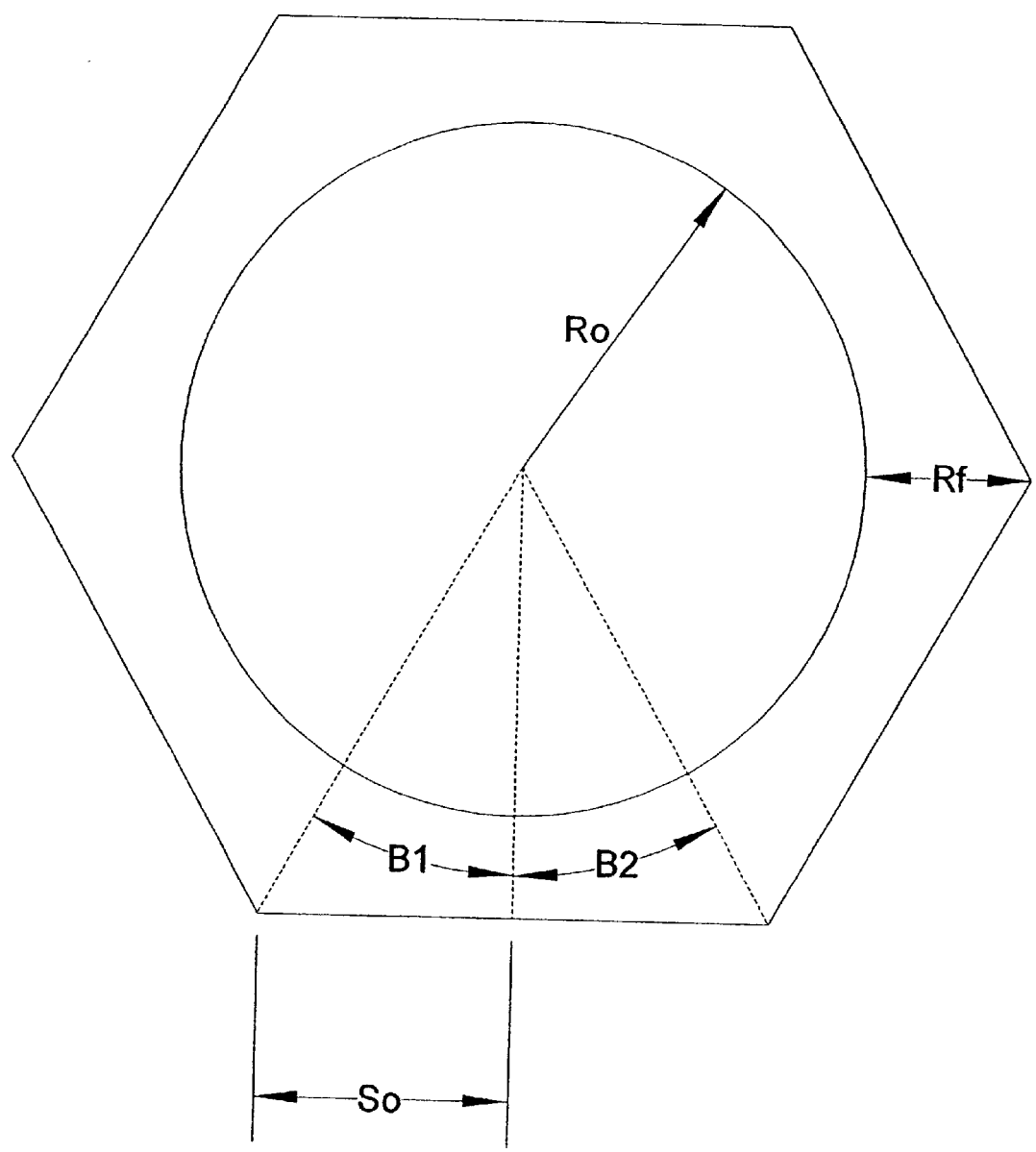
FIG. 9 shows the relationship between the mounting geometry and transducer movement according to the invention and the radial strain in the specimen under test.

A plan view schematic of the horizontal transducer system is shown in FIG. 9. In this configuration, the radial strain in a specimen under test 36 is converted to movement of the flexible cord 80 and measured with the horizontal displacement transducer. This measured displacement must be converted back to strain in the specimen under test 36 to be used for data analysis. The initial radius of the specimen under test 36 is $R_0$. During testing, there will be a change in said radius, $\Delta R$ due to deformation of the specimen in response to loading. The radius from the center of the specimen under test 36 to the point at which the flexible cord 80 changes direction (i.e. at the pivot 84), is R. There is a fixed distance, $R_F$ that accounts for the rigid, membrane-mounted fixture between $R_0$ and R. Therefore, the equation relevant to the radial movement of the instrumentation is:

$$R = R_0 + R_F + \Delta R$$

The distance $S_0$ is the initial half-sector length between two adjacent mounting points. It is assumed that the specimen under test 36 retains its circular cross section during deformation, so this distance is changed by $\Delta S$ and the angles $B_1$ and $B_2$ remain constant during the deformation in response to strain. Therefore, the overall length of this sector is:

$$S = S_0 + \Delta S$$

In the initial condition, $$\frac{S}{R} = \frac{S_0}{R_0 + R_F}$$

In the deformed condition, $$\frac{S}{R} = \frac{S_0 + \Delta S}{R_0 + R_F + \Delta R}$$

Since the ratio S/R is constant across both conditions, the following equation results for the computation of radial strain, $\epsilon_R$, in the specimen from the displacement of flexible cord 80 as recorded on the horizontal displacement transducer:

$$\epsilon_R = \frac{\Delta R}{R_0} = \frac{(S_0 + \Delta S)(R_0 + R_F)}{S_0 R_0} - \frac{R_0 + R_F}{R_0}$$

Since the only unknown on the right hand side of this equation is $\Delta S$, the strain may be computed from the transducer by taking the total transducer displacement reading, $\delta^T$, that results from the strain in the specimen under test 36, dividing by twice the number of contact points, 2N, where N=6 in FIG. 9, and then substituting into the above equation, i.e.:

$$\Delta S = \frac{\delta^T}{2N}$$

Figure 10:
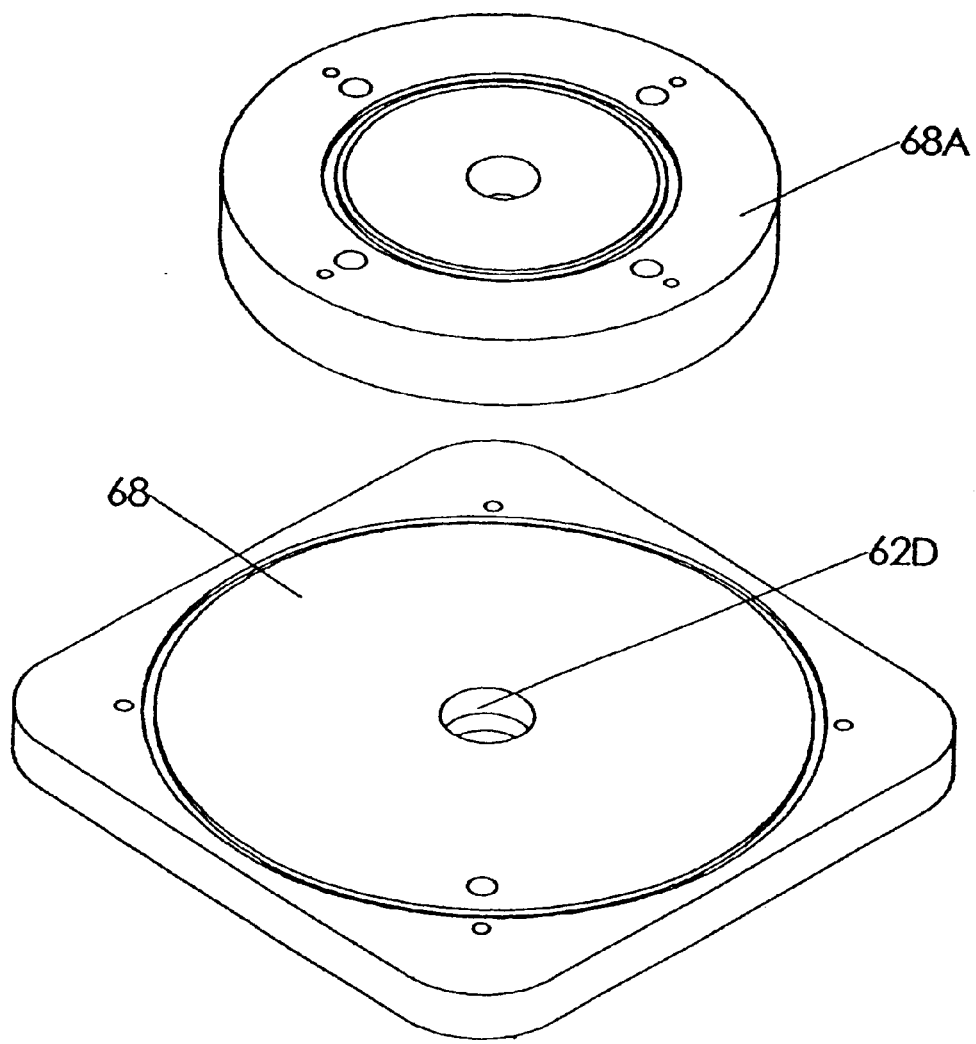
FIG. 10 shows modified retainers for the standard geotechnical triaxial module configuration.

With reference to FIG. 10, the axisymmetric triaxial assembly 18 may be replaced with a reduced number of components for standard triaxial testing. By redesigning retainer 68A and retainer 68 to seal with the reaction rod 42 and the rod of the hydraulic actuator 40, respectively, a standard geotechnical triaxial cell may be emulated. The retainers only need to have the central holes reduced in size and said holes fitted with sealing means such as o-rings 62D or oil seals which seal on the aforementioned rods. The rod seals, in combination with o-ring 62 and o-ring 62C provide a pressure seal for the pressure vessel cavity 24. All components other than the two aforementioned modified retainers, o-rings, and fasteners of the rapid triaxial assembly module configuration would be deleted in this geotechnical triaxial cell module configuration.

In operation, the upper retainer may be semi-permanently mounted to the top plate 28. However, the lower retainer, must be attached and detached once for every test. This requirement is a result of the fact that the reduced central hole and seal must be below the lower platen 38 and the hole will be smaller than the diameter of the platen. In addition, any electrical connections associated with on-specimen instrumentation must be connected and disconnected for every test. Finally, if fluid is to be used as the confining medium, the pressure vessel cavity 24 must be filled and drained once for every test. For these reasons, the emulation of a standard geotechnical triaxial cell is viable, but is not the preferred embodiment.

The load frame and pressure vessel 16 may take a different cross sectional form. The most obvious alternative embodiment is the circular cross section (annular ring). While this makes the pressure vessel capable of withstanding more internal pressure, it decreases the rigidity of the open section 22 of the load frame and reduces the overall axial capacity of the machine. Since, in general, the desired axial loads are much greater than the pressurization loads (i.e. confining pressure), the circular cross section is a viable, but not preferred, embodiment.

Figure 11:
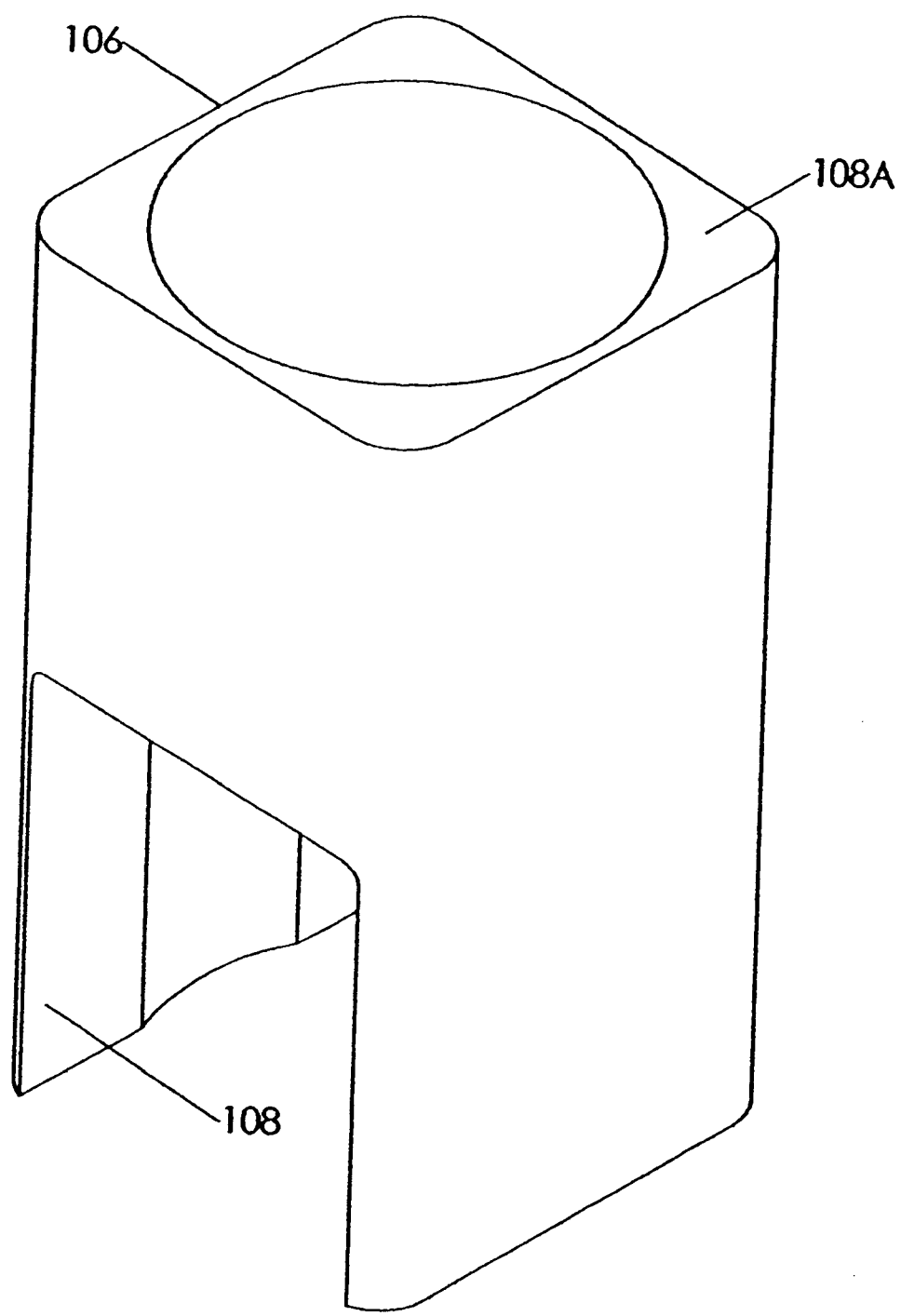
FIG. 11 is a perspective view of an alternative embodiment of the load frame and pressure vessel.

However, a hybrid cross section 106, as shown in FIG. 11, which is circular on the inside diameter, and square on the outside is a viable option that could have significant engineering advantages. This configuration could increase the maximum allowable internal pressure of the device without reducing the axial capacity of the machine. In fact, if the open space is machined such that some of the additional mass of the tubing at the corners 108 of the cross section is left intact, the axial capacity of the machine will actually increase. Another engineering advantage of this configuration is that the mass of material between the internal circular boundary and the external square shape at the corners 108A reduces the volume required for pressurization, possibly resulting in better dynamic response of the axisymmetric triaxial pressurization system. Unfortunately, this cross sectional shape is generally obtained by extrusion or by machining from solid square stock, either of which manufacturing methods would be relatively expensive compared to off-the-shelf square tubing. The additional expense would be justified if the axisymmetric pressure vessel cavity is to be pressurized to very high pressures (e.g. for testing in the rock mechanics field instead of the geotechnical and pavements field).

All cross sections may include doors on the front and back of the open section to ensure operator safety.

The operation of frames with alternative cross sections is not significantly different than the standard operation of the preferred embodiment.

It can be seen that a combined loading frame and axisymmetric triaxial pressure cell configurable for various triaxial cell functionalities and instrumentation are provided according to the invention. The preferred embodiment does not require triaxial cell fixtures which are separate from the loading frame or which must be moved or dismantled in order to change specimens. The preferred instrumentation system embodiment minimizes errors due to its own presence and the system is not self-limiting for the case of large strain movements.

Although the description above contains many specificities, these should not be construed as limiting the scope of the invention but as merely providing illustrations of some of the presently preferred embodiments of this invention. Various other embodiments and ramifications are possible within its scope. For example, the planview of the load frame and pressure vessel may be a shape other than square in cross section (e.g. round tubing). The preferred triaxial module embodiment comprising both hardware and instrumentation in combination may be replaced with a modified version of only two components of the preferred embodiment to yield a standard geotechnical triaxial cell configuration for use with or without on-specimen instrumentation. Vertical transducers may be referenced to their mounting hardware in a number of ways which may or may not cause mechanical moments to be generated as a consequence of deformations in the specimen under test. The preferred embodiment shows the inventor's assessment of the optimal number of sensors and mounting hardware positions. Alternative numbers of sensors and mounts may be used. The movement of the reaction rod may be automated. The actuator(s) and pressurization system may be pneumatic (e.g. air, nitrogen or any other gas) or alternatively are mechanical (e.g. electro-mechanically driven using devices such as servo-motors or stepper motors) instead of hydraulic (e.g. fluid), however such systems are likely to produce a reduction in performance below that obtainable with typical hydraulic systems. Transducer technology is rapidly advancing and the conversion from analog devices such as the linear variable differential transformer, LVDT, (sometimes called the linear variable displacement transducer) or capacitive or magnetic or reluctance devices to digital devices such as the rotary encoder is an integral part of that advance. Electromagnetic wave based transducers appear to be one of the promising technologies and waves in the visible and infrared portions of the spectrum are of particular interest in the short term. The rotary encoder provides some significant advantages over the LVDT in the preferred embodiment, but there may be future instrumentation sensors that may improve upon that device, and whether such devices will go back to analog or further exploit digital technology remains to be seen. Sensors other than those presented in the preferred embodiment may prove viable. At present, very long wavelength devices with three dimensional video image processing such as those used in the medical industry are too expensive and often not precise enough to be used in this application, but future systems may be available which could eliminate the need for internal sensors in favor of external non-contact sensors which measure the specimen movements directly, or by measuring the movement of membrane mounted targets similar to the instrumentation mounts presented in the preferred embodiment. The instrumentation mounts, in particular those which only provide guides for the flexible cord, can be of various geometries. The two fundamental types of mount are those which incorporate a rotating element so that as the cord moves little to no friction is applied because of the presence of a bearing element, or those which do not have a rotating element and rely on the surface properties of the cord and the mount to minimize friction. Those which do not have a rotating element would include such concepts as the well-known fishing monofilament moving through the fishing rod eyelet line guides. While a material such as commonly available fishing monofilament might be used for the flexible cord, monofilament lines sometimes have engineering properties that are not suitable for use in this application, e.g. they may stretch under small loads which would render them unusable for strain measurement or be chemically incompatible with certain fluids that might be used for applying confining pressure, or if they are selected so that they do not stretch under load, they may be so stiff that their minimum radius of curvature is too large to be useful in the preferred embodiment, even stranded stainless steel fishing leader material is susceptible to this problem.

Thus, it is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A materials testing machine comprising:
   a frame with a longitudinal axis and having a first open section adapted for unconfined testing of a specimen and a second pressurizable chamber section adapted to contain a pressurized medium for testing of said specimen;
   at least one rod movably mounted in said frame and adapted to move along said longitudinal axis, said rod movable between said first open section and said second chamber; and
   at least one load transmission means in mechanical engagement with said rod for transferring a load to said specimen;
   wherein said specimen may be axisymmetrically tested in said chamber and subjected to unconfined loading tests in said first open section.

2. The materials testing machine of claim 1 further including:
   at least one component adapted for data measurement mounted on said machine.

3. The materials testing machine of claim 2 wherein:
   said at least one component adapted for data measurement is selected from the group of electronic components, mechanical components, fluidic components or combinations thereof.

4. The materials testing machine of claim 1 wherein:

said chamber includes at least one access opening, an axisymmetric triaxial functional removable module is adapted to be placed in said chamber, said module including a tubular membrane having a first end and a second end, an upper sealing ring assembly attached to said first end and a lower sealing ring assembly attached to said second end, said membrane adapted to surround said specimen, at least one ring assembly of said module adapted to seal said access opening whereby the pressurizing medium in said chamber does not directly contact said specimen.

5. The materials testing machine of claim 4 wherein:

at least one component adapted for data measurement is mounted on said removable module.

6. The materials testing machine of claim 4 wherein said axisymmetric triaxial functional module comprises said upper and lower sealing ring assemblies having sealing connection means to prevent all-round pressurization of said specimen and enable radial pressurization of said specimen.

7. The materials testing machine of claim 1 wherein said load transmission means comprise, in combination:

one or more metal platens; and a second adjustable reaction rod for transmitting a load to said specimen when in said chamber and said open section.

8. The materials testing machine of claim 7 wherein said load transmission means comprise, in combination a second reaction rod in contact with a second platen:

at least one of said platen faced with a relatively soft or anisotropic material for minimizing restriction of radial movement of any ends of said specimen under test.

9. The material testing machine in accordance with claim 7 wherein:

said first and second platens are brush platens having a facing which includes one or more sheets of an insulating material;

whereby said specimen is maintained at a desired temperature.

10. The material testing machine in accordance with claim 9 further including:

an interface fluid between said one or more sheets for aiding in maintaining said specimen at said desired temperature.

11. The material testing machine in accordance with claim 10 further including:

means for controlling temperature of a fluid in said chamber.

12. The materials testing machine of claim 1 wherein:

said machine further includes heat exchange means adapted to establish and maintain said specimen at a particular temperature.

13. The materials testing machine of claim 12 wherein said heat exchange means comprises, in combination:

one or more platens adapted to provide a barrier to heat exchange; and at least one controlled temperature pressure transmission means.

14. The materials testing machine of claim 1 further including: an access opening to said chamber; and sealing means for installing and removing interchangeable axisymmetric triaxial functional and instrumentation modules through said access opening.

15. The materials testing machine of claim 1 further including:

heat exchange means adapted to establish and maintain said specimen at a particular temperature.

16. The materials testing machine of claim 1 further including:

an attachment plate between said chamber and said open section permanently attached to said frame, an access opening in said plate, said access opening adapted to be sealed by an axisymmetric triaxial functional module containing a specimen.

17. A materials testing machine comprising:

a loading frame of a finite length, said loading frame having a first open section extending along a first part of its length adapted for unconfined testing of a specimen and a second pressurizable chamber extending over a remaining part of its length and defining therein a pressure vessel cavity, said cavity adapted for pressurized testing of said specimen;

at least one pressure vessel cavity access means;

one or more interchangeable axisymmetric triaxial functional modules including a rapid triaxial cell assembly module with sealing means, said sealing means having sealing connection means adapted to prevent all-around pressurization of said specimen under test and enable radial pressurization of said specimen, wherein said sealing connection means is a flexible membrane tube; and at least one load transmission means in mechanical engagement with said loading frame for transferring a load to said specimen under test;

wherein pressurized and unconfined load testing are therein enabled.

18. A materials testing machine comprising:

a loading frame of a finite length, said loading frame having a first open section extending along a first part of its length adapted for unconfined load testing of a specimen and a second pressurizable chamber extending over a remaining part of its length and defining therein a pressure vessel cavity, said cavity adapted for pressurized fluidic testing of said specimen;

at least one pressure vessel cavity access means;

one or more interchangeable axisymmetric triaxial functional modules including, in combination, a rapid triaxial cell assembly module with upper and lower sealing ring assemblies, said sealing ring assemblies having a flexible sealing connection adapted to prevent all-around pressurization of said specimen and enable radial pressurization of said specimen; and instrumentation means; and at least one load transmission means in mechanical engagement with said loading frame for transferring a load to said specimen;

at least one of said upper and lower ring assemblies adapted to seal said pressure cavity access means;

wherein pressurized and unconfined testing are therein enabled.

19. A materials testing machine for conducting two different tests on a specimen, said machine comprising an integral elongated frame, said frame having an enclosed chamber portion with an inner pressure vessel cavity and an open unconfined testing portion, said chamber portion having a sealable access opening, an axisymmetric testing module removably enclosed in said chamber, a load transmission device for applying a load to a specimen, said load transmission device in mechanical contact with one end of an actuator, the other end of said actuator located outside said chamber, said actuator movably mounted in said open unconfined testing space, said actuator adapted to apply a load in said open unconfined testing space and extend into said chamber.

20. The materials testing machine of claim 19 further comprising a reaction rod mounted on said chamber and extending into said pressure vessel cavity, said reaction rod adapted to extend through said pressure vessel cavity into said open unconfined testing space.

* * * * *